(12) United States Patent
Kuo-Long

(10) Patent No.: US 6,355,095 B1
(45) Date of Patent: Mar. 12, 2002

(54) DC/AC AIR CLEANER FOR A VEHICLE

(76) Inventor: Huang Kuo-Long, No. 320, Nan-Kung Street, Yung-Kang, Tainan Hsien (TW)

( * ) Notice: Subject to any disclaimer, the term of this patent is extended or adjusted under 35 U.S.C. 154(b) by 0 days.

(21) Appl. No.: 09/576,333

(22) Filed: May 22, 2000

(51) Int. Cl.$^7$ ................................................ B03C 3/72
(52) U.S. Cl. .............................. 96/26; 55/385.3; 96/58; 96/63; 96/83; 96/84; 96/97
(58) Field of Search ................. 96/97, 63, 83, 96/84, 26, 57, 58; 55/385.3

(56) References Cited

U.S. PATENT DOCUMENTS

| | | | | |
|---|---|---|---|---|
| 5,290,342 A | * | 3/1994 | Morita et al. | 96/83 X |
| 5,407,469 A | * | 4/1995 | Sun | 96/63 X |
| 5,578,113 A | * | 11/1996 | Glenn | 96/57 X |
| 5,656,063 A | * | 8/1997 | Hsu | 96/58 X |
| 5,702,507 A | * | 12/1997 | Wang | 96/63 X |
| 5,707,429 A | * | 1/1998 | Lewis | 96/63 |
| 5,759,239 A | * | 6/1998 | Yu | 96/63 X |
| 5,820,660 A | * | 10/1998 | Ko | 96/97 X |
| 6,126,727 A | * | 10/2000 | Lo | 96/97 X |

* cited by examiner

Primary Examiner—Richard L. Chiesa
(74) Attorney, Agent, or Firm—ALan Kamrath; Rider, Bennett, Egan & Arundel, LLP

(57) ABSTRACT

A DC/AC air cleaner for a vehicle includes a chassis having a bottom plate and two side plates formed on two sides of the bottom plate, respectively. An insertion slot is defined in the bottom plate, and two inner plates are mounted between the side plates and configured to define a clamping slot, a positioning slot, and an engaging slot. A lower end of a face plate is held by the insertion slot. A lower end of an activated filtering mesh is held by the clamping slot. A lower end of a static discharger is held by the positioning slot, and the lower end of a fan is held by the engaging slot. An upper cover is provided to retain the upper end of the face plate, upper end of the activated filtering mesh, upper end of the static discharger, and upper end of the fan.

4 Claims, 4 Drawing Sheets

DC/AC AIR CLEANER FOR A VEHICLE

BACKGROUND OF THE INVENTION

1. Field of the Invention

The present invention relates to a DC/AC air cleaner for a vehicle.

2. Description of the Related Art

Air pollution becomes more and more serious. A car driver and the passenger(s) in a car must withstand poor air quality if the car windows are opened. If the car windows are all closed, the air quality in the isolated space in the car is also intolerable. The present invention is intended to provide a DC/AC air cleaner for a vehicle to solve this problem.

SUMMARY OF THE INVENTION

In accordance with the present invention a DC/AC air cleaner for a vehicle comprises:

a chassis including a bottom plate and two side plates formed on two sides of the bottom plate, respectively, an insertion slot being defined in the bottom plate, two inner plates being mounted between the side plates and configured to define a clamping slot, a positioning slot, and an engaging slot, a circuit board mounted to the bottom plate, a face plate having a lower end held by the insertion slot and an upper end, an activated filtering mesh having a lower end held by the clamping slot and an upper end, a static discharger having a lower end held by the positioning slot and an upper end, a fan having a lower end held by the engaging slot and an upper end, and an upper cover for retaining the upper end of the face plate, the upper end of the activated filtering mesh, the upper end of the static discharger, and the upper end of the fan.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
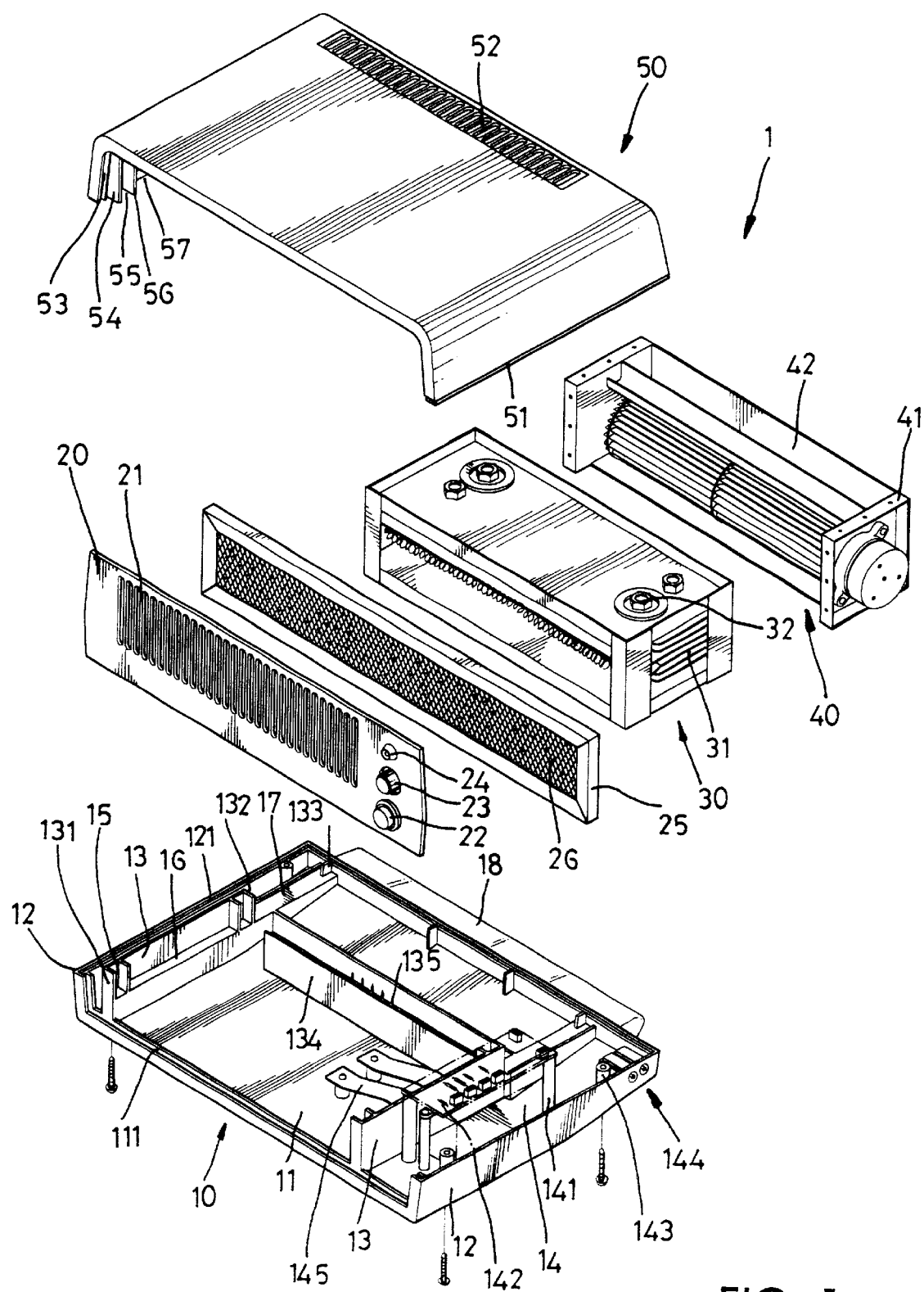
FIG. 1 is an exploded perspective view of a DC/AC air cleaner in accordance with the present invention.
Figure 2:
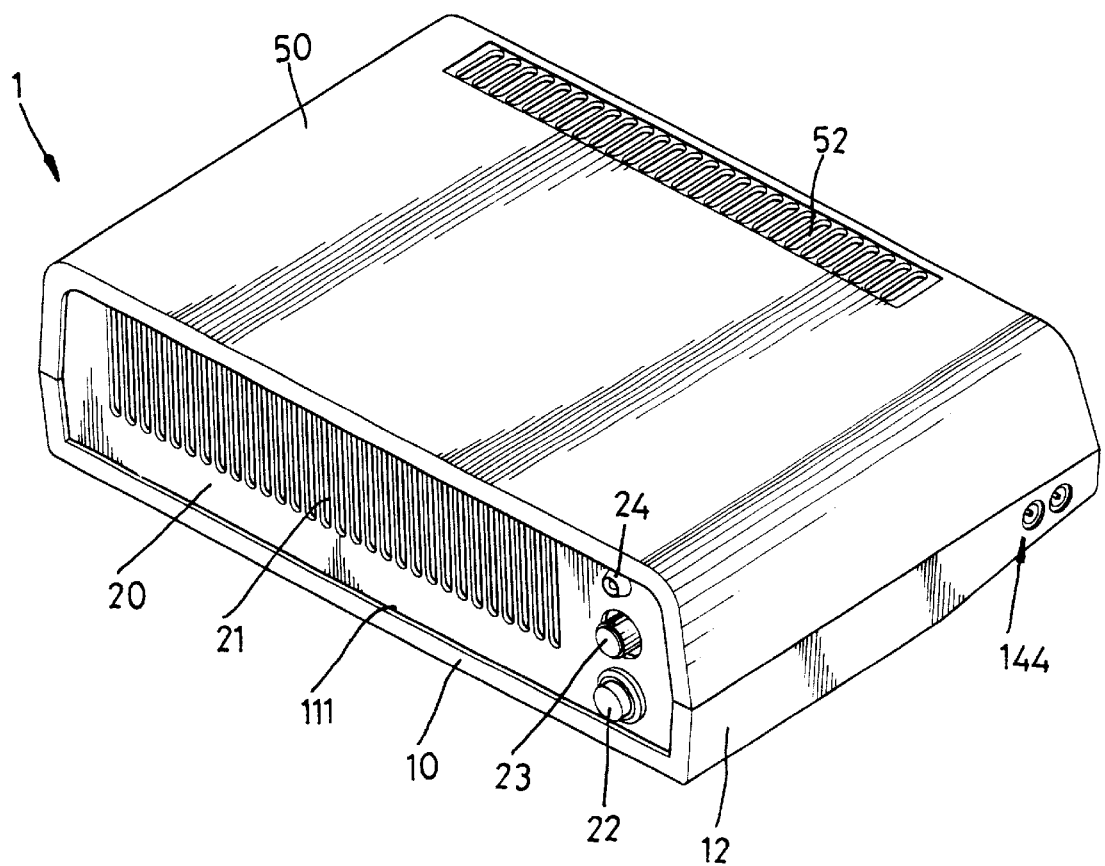
FIG. 2 is a perspective view of the DC/AC air cleaner in accordance with the present invention.
Figure 3:
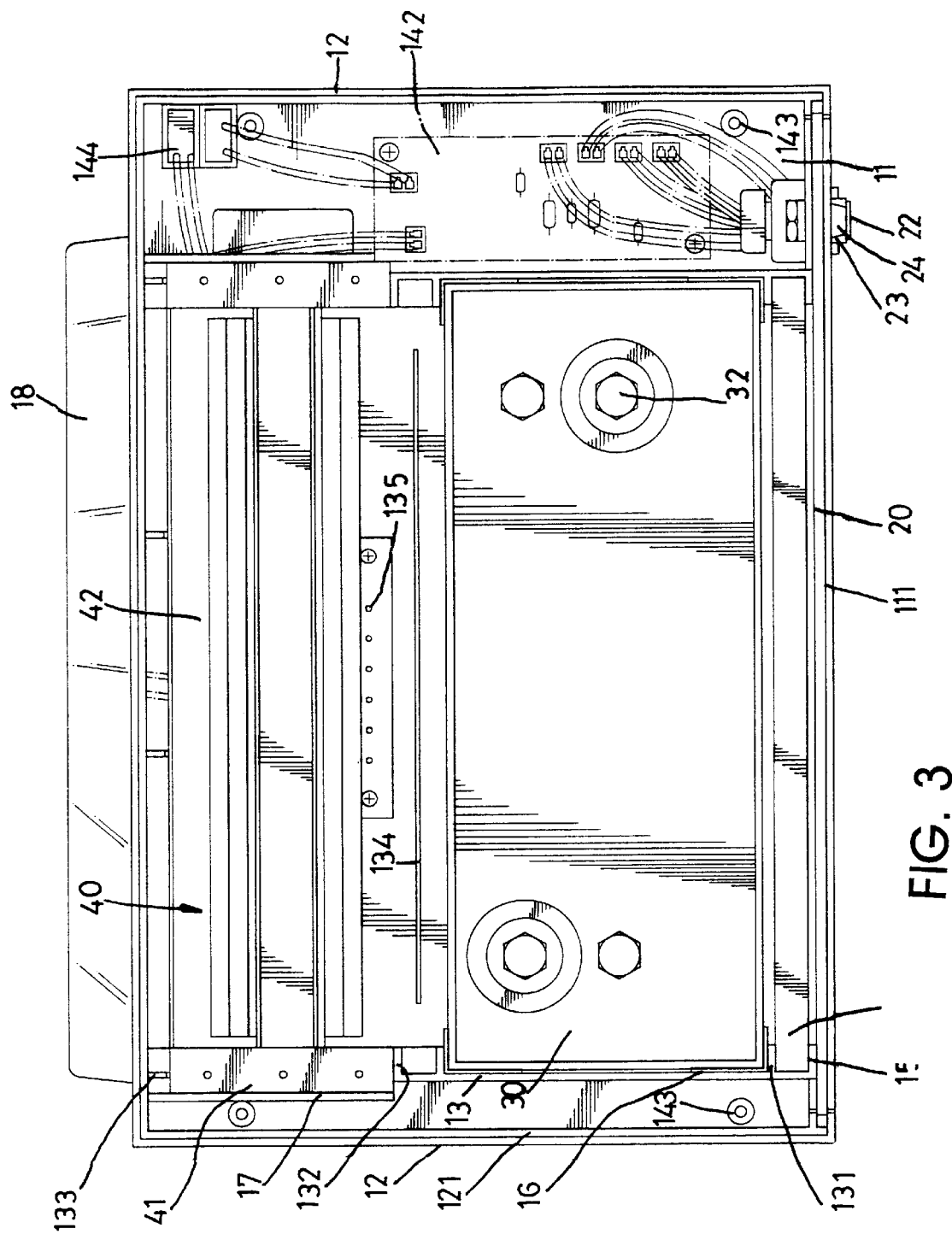
FIG. 3 is a top view of the DC/AC air cleaner in accordance with the present invention, wherein the upper cover is removed for clarity.

Referring to FIGS. 1 through 3, a DC/AC air cleaner 1 in accordance with the present invention generally includes a chassis 10, a face plate 20, an activated carbon filtering mesh 26, a static discharger 30, a fan 40, and an upper cover 50. The chassis 10 includes a bottom plate 11, two side plates 12 formed on two sides of the bottom plate 11, respectively, and two inner plates 13 disposed on the bottom plate 11. One of the inner plate 13 and an adjacent side plate 12 together define a compartment 14 in which a number of posts 141 are mounted. A circuit board 142 is supported at top of the posts 141. A socket 144 is provided in a rear of the compartment 14 to allow insertion of power lines.

An insertion slot 111 is defined in a front end of the bottom board 11 for positioning a lower end of the face plate 20. Rib plates 131 and 132 and a block 133 are attached to each inner plate 13, thereby defining a clamping slot 15, a positioning slot 16, and an engaging slot 17 in the inner plate 13 (the left one in FIG. 3). By such an arrangement, the lower end of the face plate 20 is directly inserted into the insertion slot 111, a lower end of a frame 25 of the activated carbon filtering mesh 26 is inserted into the clamping slot 15, a lower end of the static discharger 30 is inserted into the positioning slot 16, and a lower end of a frame 41 of the fan 40 is inserted into the engaging slot 17. All of the elements are thus positioned.

The side plates 12 (the left one in FIG. 3) on the bottom plate 10 define a U-shape groove 121, and the upper cover 50 includes a U-shape protrusion 51 so as to be received in the U-shape groove 121, thereby positioning the upper cover 50. The upper cover 50 further includes two rib plates 54 and 56 to define an insertion slot 53, a clamping slot 55, and a positioning slot 57 for clamping an upper end of the face plate 20, upper end of the frame 25 of the activated carbon filtering mesh 26, and upper end of the static discharger 30, respectively. Upper end of the frame 41 of the fan 40 is held in place by an underside of the upper cover 50 from which the rib plates 54 and 56 project downwardly. By such an arrangement, all of the elements for filtration can be positioned between the chassis 10 and the upper cover 50.

Referring to FIGS. 1 and 3, the face plate 20 includes a plurality of air holes 21, a switch 22, a knob 23, and an indication lamp 24. The switch 22, knob 23, and indication lamp 24 are connected to a circuit board 142 by wires. The socket 144 and the fan 40 as well as power source for driving the fan 40 are also electrically connected to the circuit board 142. Positive and negative pole plates 145 are mounted to the chassis 10 and in contact with positive and negative poles 32 of the static discharger 30. Also disposed on the chassis 10 is a separation plate 134, and a row of discharging pins 135 are mounted between the separation plate 134 and the engaging slot 17. The static discharger 30 includes a plurality of layers of static dust-collecting board 31. The high voltage between the poles 32 is fed to each layer of static dust-collecting board 31, thereby generating a magnetic field between each two adjacent layers of static dust-collecting board 31. A third brake lamp 18 may be mounted to a rear of the chassis 10.

Figure 4:
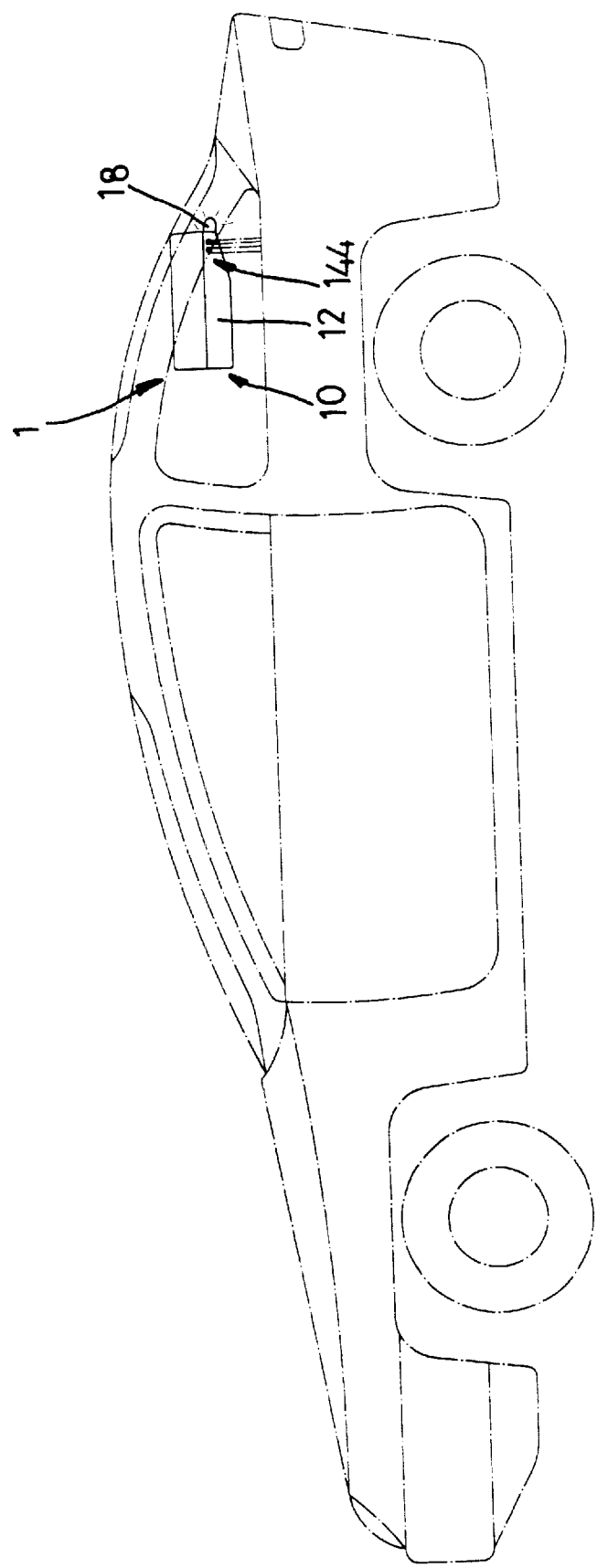
FIG. 4 is a schematic view illustrating mounting of the DC/AC air cleaner to a car.

The air cleaner of the present invention can be mounted to a rear seat area of a car and located adjacent to the rear windshield, best shown in FIG. 4. The socket 144 may be inserted by a vehicle power source. The lamp 18 is connected to the brake control system of the car, thereby acting as a third brake lamp for the car.

When in use, referring to FIG. 1, the fan 40 is activated to turn for drawing air into the air cleaner 1 via the air holes 21 in the face plate 20. The air drawn into the air cleaner 1 is firstly filtered by the activated carbon filtering mesh 26 to remove larger particles in the air. The air is then moved into the magnetic fields in the static discharger 30. The discharging pins 135 of the static discharger 30 may decompose smaller particles in the air and generates a large amount of negative ions in the air which are then fed out via the outlets 42, thereby filtering the air inside the car.

Although the invention has been explained in relation to its preferred embodiment, it is to be understood that many other possible modifications and variations can be made without departing from the spirit and scope of the invention as hereinafter claimed.

What is claimed is:

1. A DC/AC air cleaner for a vehicle, comprising:

chassis (10) including a bottom plate (11) and two side plates (12) formed on two sides of the bottom plate, respectively, an insertion slot (111) being defined in the bottom plate, two inner plates (13) being mounted between the side plates (12) and configured to define a clamping slot (15), a positioning slot (16), and an engaging slot (17), a circuit board (142) mounted to the bottom plate, a face plate (20) having a lower end held by the insertion slot (111) and an upper end, an activated filtering mesh (26) having a lower end held by the clamping slot (15) and an upper end, a static discharger (30) having a lower end held by the positioning slot (16) and an upper end, a fan (40) having a lower end held by the engaging slot (17) and an upper end, and an upper cover (50) for retaining the upper end of the face plate (20), the upper end of the activated filtering mesh (26), the upper end of the static discharger (30), and the upper end of the fan (40).

2. The DC/AC air cleaner for a vehicle as claimed in claim 1, wherein the upper cover (50) includes an underside that is configured to define a second insertion slot (53), a second clamping slot (55), and a second positioning slot (57) for holding the upper end of the face plate (20), the upper end of the activated filtering mesh (26), the upper end of the static discharger (30), respectively.

3. The DC/AC air cleaner for a vehicle as claimed in claim 1, wherein the bottom plate (11) further comprises a separation plate (134) formed thereon, a row of discharging pins (135) being mounted between the separation plate (134) and the engaging slot (17).

4. The DC/AC air cleaner for a vehicle as claimed in claim 1, further comprising a third brake lamp (18) mounted to the chassis (10), the third brake lamp being adapted to be electrically connected to a brake control system of a vehicle.

* * * * *